US00PP18057P2

(12) United States Plant Patent
Olesen

(10) Patent No.: US PP18,057 P2
(45) Date of Patent: Sep. 18, 2007

(54) HYBRID TEA ROSE PLANT NAMED 'POULPMT005'

(50) Latin Name: ***Rosa* hybrid**
Varietal Denomination: Poulpmt005

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,462

(22) Filed: Mar. 23, 2006

(51) Int. Cl.
*A01H 5/00* (2006.01)

(52) U.S. Cl. ..... Plt./134
(58) Field of Classification Search ..... Plt./134
See application file for complete search history.

*Primary Examiner*—Kent Bell
*Assistant Examiner*—June Hwu

(57) ABSTRACT

A new garden rose plant of the hybrid tea class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpmt005'.

SUMMARY OF THE CLAIMED PLANT

The present discovery constitutes a new and distinct variety of rose plant of the hybrid tea class which was discovered in a cultivated area.

The new rose variety resulted from a naturally occurring mutation of unknown causation on a branch of 'Poulrim', U.S. Plant Pat. No. 12,465. The resulting mutation was selected in 1989 and evaluations were conducted on the resulting rose plants in a controlled environment.

The rose plant of the present discovery has a unique combination of characteristics which are outstanding in the new variety and which distinguish it from the original rose 'Poulrim'. The claimed plant is distinguishable from the parent plant mainly by flower color. While 'Poulrim' has flowers which are generally orange in color, 'Poulpmt005' has yellow flowers.

The criteria used to evaluate the claimed plant were selected in order to introduce a distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpmt005' from all other varieties of which we are aware.

Asexual reproduction of 'Poulpmt005' by cuttings was first done by Mogens N. Olesen in Fredensborg, Denmark, in July of 1989. This initial and other subsequent propagations have demonstrated that the characteristics of 'Poulpmt005' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpmt005'. Specifically illustrated in the drawing are.

DETAILED DESCRIPTION OF THE VARIETY

Figures 1A, 1B, 1C:
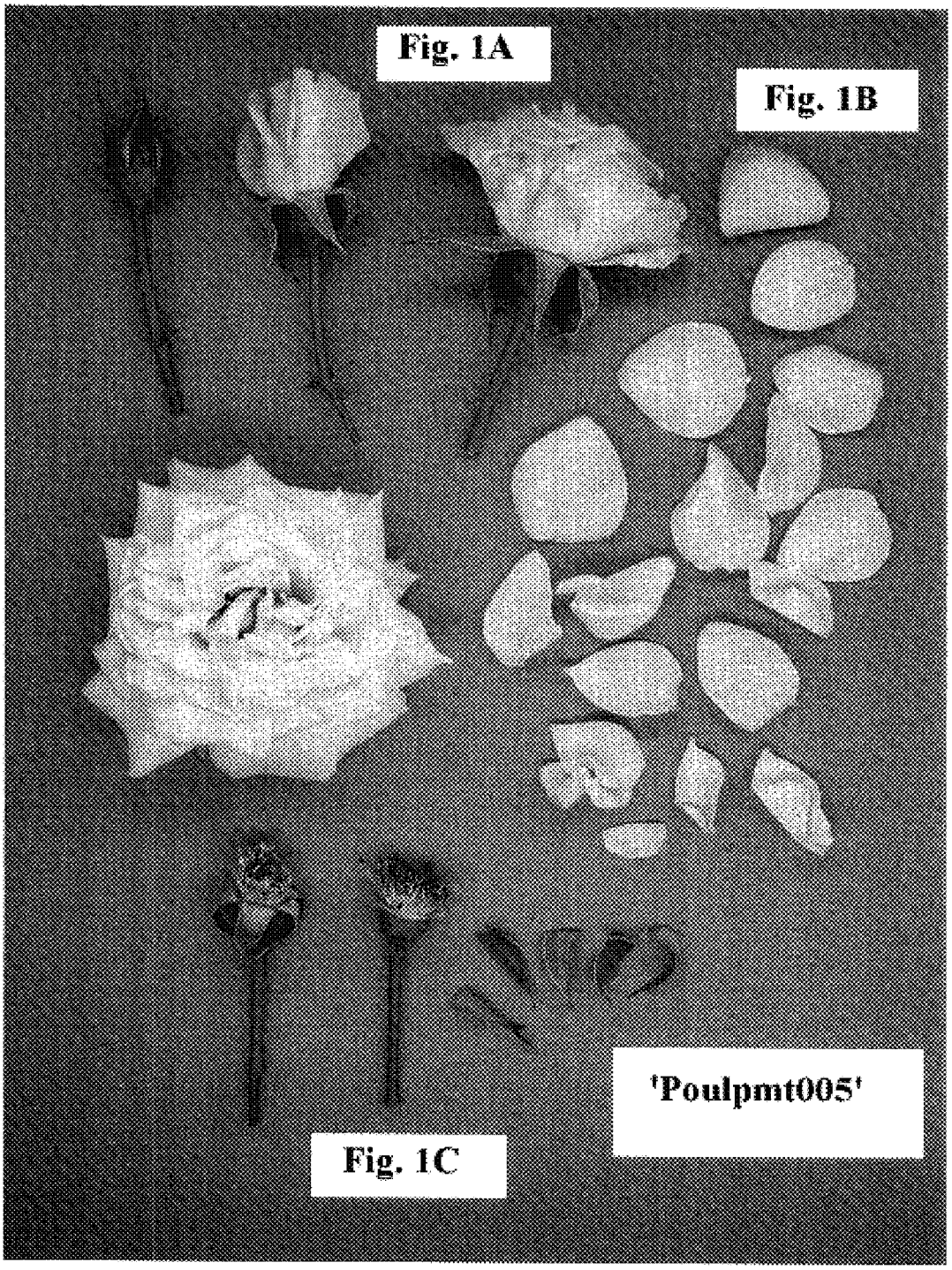
FIG. 1A; Flower bud closed and flowers at various stages of development.
FIG. 1B; Flower petals, detached.
FIG. 1C; Sepals, receptacle, reproductive flower parts, and peduncle.
Figures 2A, 2B, 2C, 2D:
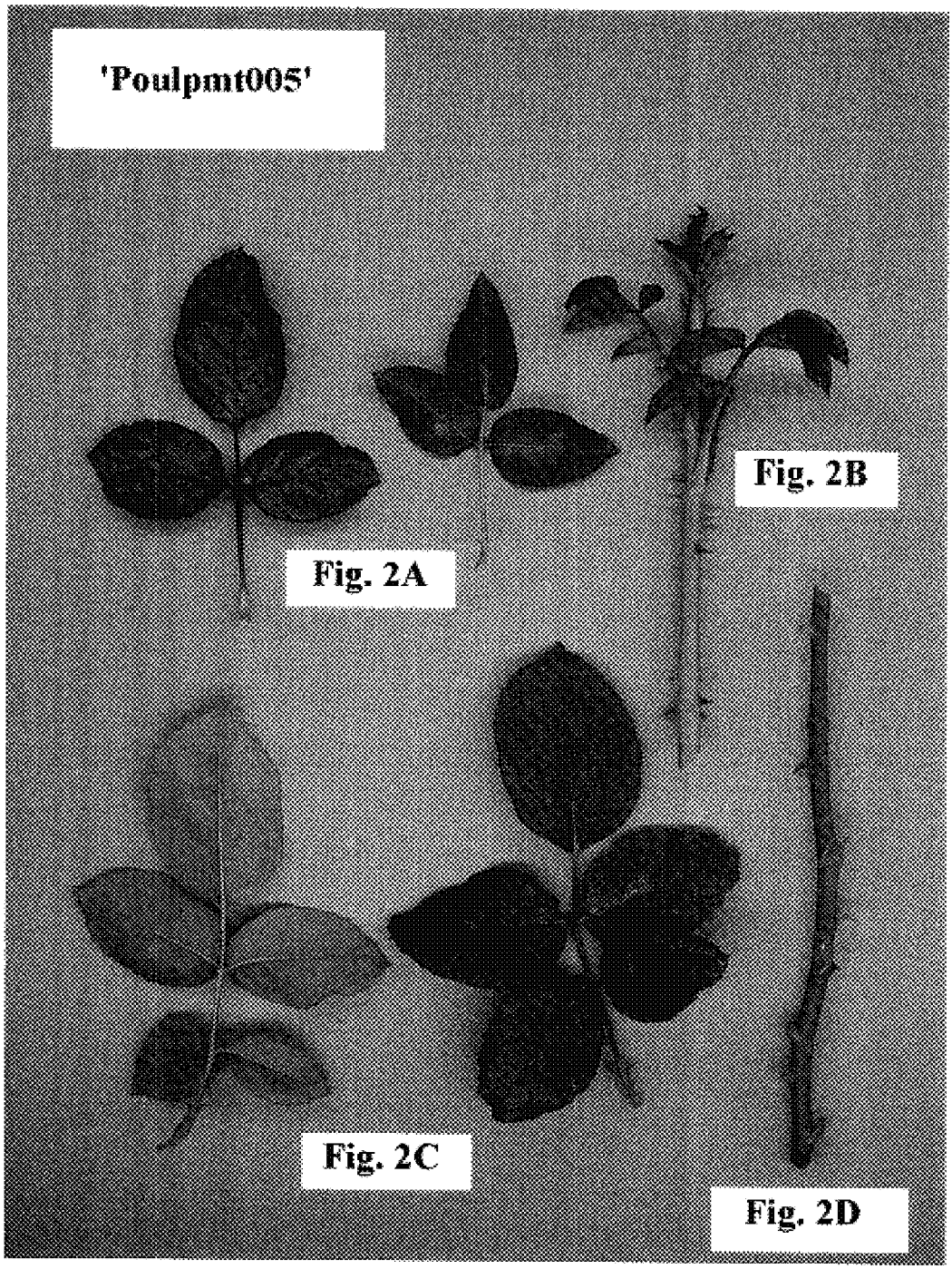
FIG. 2A; Juvenile leaves.
FIG. 2B; Juvenile growth and bare stem, exhibiting thorns.
FIG. 2C; Mature leaves.
FIG. 2D; Bare stem exhibiting thorns.

The following is a description of 'Poulpmt005', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulpm003', U.S. Plant Pat. No. 15,385, are compared to 'Poulpmt005' in Chart 1.

CHART 1

| | 'Poulpmt005' | 'Poulpm003' |
|---|---|---|
| Petal Count | 33 petals total, 5 to 8 of which are petaloids | 30 |
| Flower dimensions | 70 mm diameter by 35 mm in depth | 80 mm diameter by 40 mm depth |
| General Tonality of Flower Color | Yellow Group 4B at the periphery and Yellow Group 7C toward flower center | Yellow Group 4D |

FLOWER AND FLOWER BUD

Blooming habit: Recurrent.
Flower bud:

*Size.*—Upon opening, 26 mm in length from base of receptacle to end of bud. Bud diameter is 16 mm.

*Bud form.*—Ovate.

*Bud color.*—As sepals unfold, petals are Green-Yellow Group 1C.

*Sepal inner surface.*—Color: Green Group 137B and Yellow-Green Group 144B. Surface: Strong pubescence observed.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—Normally 35 mm long by 10 mm wide.

*Receptacle.*—Texture: Smooth and lightly glabrous. Shape: Urn-shaped. Size: Normally 12 mm (h)×14 mm (w). Color: Yellow-Green Group 144A.

*Peduncle.*—Surface: Somewhat rough. Length: 45 to 55 mm. Diameter: 3.5 mm on average. Color: Yellow-Green Group 144A.

Flower bud development: Flower buds are normally borne singularly.

Flower bloom:

*Fragrance.*—Medium rose scent.

*Duration.*—The blooms have a duration on the plant of approximately 7 to 10 days. Petals do not fall cleanly away from plant after flowers have fully matured.

*Size.*—Flower diameter is 70 mm when open. Flower depth is 35 mm.

*Flower shape.*—General shape is high-centered, with a high-pointed center which is tightly closed.

*Shape of flower, side view.*—Upon opening the upper portion is flat. The lower portion is convex. After opening, the upper portion is flattened convex. The lower portion is concave.

*Petalage.*—Under normal conditions, flowers have 33 petals total, 5 to 8 of which are petaloids.

*Petal color.*—Upon opening, outer petals Upper surface: Yellow Group 7D. Lower surface: Yellow Group 6D. Upon opening, inner petals: Upper surface: Yellow Group 7C. Lower surface: Yellow Group 6D. Basal petal spots, upon opening: Upper surface: Yellow Group 7A. Lower surface: Yellow Group 6A. After opening, outer petals Upper surface: Yellow Group 8C. Lower surface: Yellow Group 8D. After opening, inner petals: Upper surface: Yellow Group 8C. Lower surface: Yellow Green 8D. Basal petal spots, after opening: Upper surface: Yellow Group 7C. Lower surface: Yellow Group 8B.

General tonality: On open flower Yellow Group 4B at the periphery and Yellow Group 7C toward flower center. No change in the general tonality at the end of the $8^{th}$ day. Afterwards, general tonality is Yellow Group 4C.

Petals:

*Petal reflex.*—Strongly.

*Margin.*—Entire and uniform. Occasionally there is a point at the center of the margin.

*Shape.*—Generally narrow elliptical to broad elliptical. Apex shape: Orbicular. Base shape: Acute.

*Size.*—Normally 38 mm (l)×33 mm (w).

*Texture.*—Smooth.

*Thickness.*—Average.

*Arrangement.*—Formal.

Petaloids:

*Quantity.*—5 to 8.

*Shape.*—Narrow elliptical.

*Color.*—Upper surface: Yellow Group 7C. Lower surface: Yellow Group 6D.

*Size.*—30 mm (l)×20 mm (w) on average.

Reproductive organs:

*Pollen.*—None observed.

*Anthers.*—Size: 3 to 3.5 mm in length. Color: Yellow Group 4B with margins of Greyed-Orange Group 163A. Quantity: 151 on average.

*Filaments.*—Color: Yellow Group 13A. Length: 10 mm on average.

*Pistils.*—Length: 8 mm on average. Quantity: 130 on average.

*Stigmas.*—Inferior in location relative to the length of the filaments and the height of the anthers. Color: Greyed-Yellow Group 161B.

*Styles.*—Color: Yellow-Green Group 145D at base; Red-Purple Group 57A toward the stigma.

*Hips.*—None Observed in the field nursery in Jackson County Oreg.

PLANT

Plant growth: Upright, somewhat compact for a hybrid tea, and bushy. When grown as a budded field grown plant on *Rosa multiflora* understock, the height of the plant is 60 to 100 cm. Average spread is 75 cm.

Stems:

*Color.*—Juvenile growth: Yellow-Green Group 146D. Mature growth: Yellow-Green Group 146A.

*Length.*—On average, canes are 60 cm from the base of the plant to the flowering portion.

*Diameter.*—4 to 8 mm.

*Internodes.*—On mature canes, there is an average distance of 45 mm between nodes.

*Surface texture.*—Young wood: Smooth. Older wood: Smooth.

Prickles:

*Incidence.*—8 prickles per 10 cm of stem.

*Size.*—Prickles on mature stems are 7 to 9 mm.

*Shape.*—Upper side: Convex. Lower side: Concave.

*Color.*—Juvenile prickles: Greyed-Yellow Group 160A with intonations of Greyed-Red 181B.

Plant foliage: Normal number of leaflets in middle of the stem: 5 leaflets.

*Compound leaf.*—Normally 150 mm (l)×110 (w).

*Quantity.*—2 leaves per 10 cm of stem on average.

*Color of mature foliage.*—Upper side: Yellow-Green Group 146A to 147A. Lower side: Yellow-Green Group 146C.

*Color of juvenile foliage.*—Yellow-Green Group 144A with generalized anthocyanic intonations of Greyed-Purple Group 184A.

Plant leaves and leaflets:

*Stipules.*—Size: 15 mm in length. Shape: Linear, slightly broad based with outward extending apecies. Margins: Finely serrated with stipitate glands. Color: Yellow-Green Group 144A.

*Petiole.*—Length: 30 to 35 mm. Diameter: 2 mm.

*Upper surface.*—Color: Yellow-Green Group 146A.

*Lower surface.*—Color: Yellow-Green Group 145A. Observations: Numerous stipitate glands, prickles and rough undersurface observed.

*Rachis.*—Length: 35 to 40 mm. Upper surface: Color: Yellow-Green Group 146A.

*Lower surface.*—Color: Yellow-Green Group 145A. Observations: Numerous stipitate glands, prickles and rough undersurface observed.

*Leaflet*.—Edge: Serrated. Size: The terminal leaflets on normal leaves are 70 to 75 mm in length by 47 to 50 mm wide. Shape: Ovate. Base: Rounded. Apex: Acuminate. Texture: Rugose. Thickness: Average. Arrangement: Odd pinnate. Venation: Reticulate. Glossiness: Somewhat glossy.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the hybrid tea rose class named 'Poulpmt005', substantially as illustrated and described herein, due to its abundant yellow flowers, disease resistance, and extended period of bloom.

* * * * *

'Poulpmt005'

'Poulpmt005'